United States Patent [19]

Kobrehel et al.

[11] 4,328,334

[45] May 4, 1982

[54] 11-AZA-10-DEOXO-10-DIHYDROERYTHROMYCIN A AND DERIVATIVES THEREOF AS WELL AS A PROCESS FOR THEIR PREPARATION

[75] Inventors: Gabrijela Kobrehel; Gordana Radobolja; Zrinka Tamburasev; Slobodan Djokic, all of Zagreb, Yugoslavia

[73] Assignee: PLIVA Pharmaceutical and Chemical Works, Zagreb, Yugoslavia

[21] Appl. No.: 134,816

[22] Filed: Mar. 28, 1980

[30] Foreign Application Priority Data

Apr. 2, 1979 [YU] Yugoslavia .............................. 768/79

[51] Int. Cl.$^3$ ...................... A61K 31/71; C07H 17/08

[52] U.S. Cl. ........................................ 536/7.4; 424/180
[58] Field of Search .............................................. 536/9

[56] References Cited

U.S. PATENT DOCUMENTS 3,478,014 11/1969 Djokic et al. ............................ 536/9
3,574,185 4/1971 Tamburasev et al. .................. 536/9
3,652,537 3/1972 Massey et al. .......................... 536/9

*Primary Examiner*—Johnnie R. Brown
*Attorney, Agent, or Firm*—Pollock, Vande Sande & Priddy

[57] ABSTRACT

11-aza-10-deoxo-10-dihydroerythromycin A and derivatives thereof, and process for preparation thereof.

24 Claims, No Drawings

11-AZA-10-DEOXO-10-DIHYDROERYTHROMYCIN A AND DERIVATIVES THEREOF AS WELL AS A PROCESS FOR THEIR PREPARATION

The invention relates to novel compounds from the class of erythromycins with antibacterial action, i.e. 11-aza-4-0-cladinosyl-6-0-desosaminyl-15-ethyl-7,13,14-trihydroxy-3,5,7,9,12,14-hexamethyloxacyclopentadecane-2-one (11-aza-10-deoxo-10-dihydroerythromycin A) as well as its acyl derivatives and N-(4-R-benzenesulfonyl) derivatives of the general formula

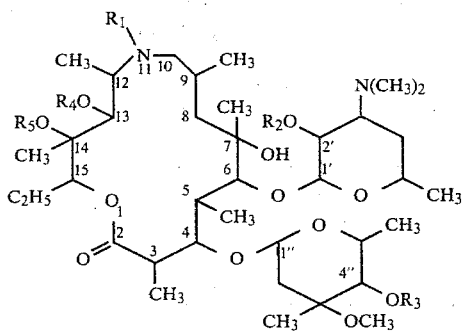

wherein
$R_1$ represents a hydrogen atom, an acyl group or a 4—R—$C_6H_4$—$SO_2$—group, wherein R represents an alkyl, halogen or acyl amino group, and
$R_2$, $R_3$, $R_4$ and $R_5$, which can be the same or different, represent a hydrogen atom or an acyl group, or $R_4$ and $R_5$ together have the meaning of >CO group,
as well as to a process for the preparation of the former by means of Beckmann rearrangement of erythromycin A oxime followed by reduction of the product so obtained and to a process for the preparation of its acyl derivatives and N-(4-R-benzenesulfonyl) derivatives.

It is well known that under the influence of strong acids, ketoximes are rearranged to carbamides and in cyclic systems to lactames, respectively, (Houben-Weyl Bd. VII/2b, 1986, 1976; Org. Reactions 11, 1, 1960; J. Org. Chem. 37, 2035, 1972; J. Org. Chem. 37, 3961, 1972).

It is also well known that a conventional way for Beckmann rearrangement is the in situ preparation of O-arylsulfoesters of ketoximes, especially of p-toluenesulfonates, which are immediately further rearranged in an aqueous medium to the corresponding lactam (J. Am. Chem. Soc. 72, 5323, 1950; J. Am. Chem. Soc. 77, 1094, 1955).

It is further known that, by using a solvent, that may act nucleophilically, instead of water, the rearrangement is stopped at the imine step, whereby O-alkyl- and O-aryl-imino ethers, amidines, sulfamidines (J. Chem. Soc., 1514, 1948; J. Am. Chem. Soc. 80, 5880, 1958), O-imidylphosphates (Chemistry and Industry 1183, 1955) and tetrazoles (J. Org. Chem. 15, 58, 1950) can be prepared.

Now we have found that 11-aza-10-deoxo-10-dihydroerythromycin A can be prepared by means of Beckmann rearrangement of erythromycin A oxime with aromatic sulfochlorides, whereupon the obtained product is isolated and subjected to reduction. The structure of the new compound is represented by formula I

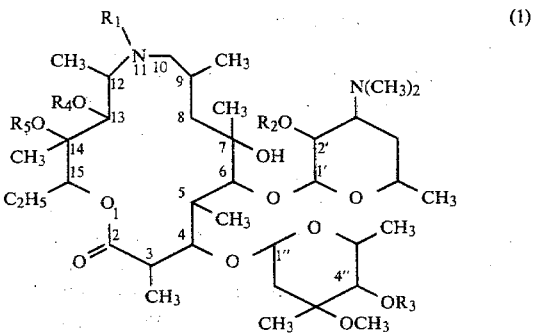

Compound I: $R_1$, $R_2$, $R_3$, $R_4$, $R_5$=H
Compound II: $R_1$ and $R_2$=acyl, $R_3$, $R_4$, $R_5$=H
Compound III: $R_1$, $R_2$, $R_3$=acyl, $R_4$, $R_5$=H
Compound IV: $R_1$, $R_2$, $R_3$, $R_4$=acyl, $R_5$=H
Compound V: $R_1$=acyl, $R_2$, $R_3$, $R_4$, $R_5$=H
Compound VI: $R_1$, $R_2$, $R_3$=H, $R_4$, $R_5$=>C=O
Compound VII: $R_1$, $R_2$, $R_3$=acyl, $R_4$, $R_5$=C=O
Compound VIII: $R_1$=4—R—$C_6H_4$—$SO_2$—, $R_2$, $R_3$, $R_4$, $R_5$=H.

According to the present invention the Beckmann rearrangement or erythromycin A oxime is carried out with 1 to 2 moles of sulfochlorides of the formula 4—R—$C_6H_4$—$SO_2Cl$, wherein R represents alkyl, halogen or acylamino group, and 2 and 4 moles of alkali metal salts, e.g. $NaHCO_3$, at 5° C. in an acetone-water mixture or in any other suitable solvent.

After the accomplished reaction (about 4 hours) acetone is evaporated under reduced pressure and the obtained aqueous suspension is extracted at pH 5.5, 6.0 and 8.0 with chloroform or some other solvent. The combined extracts at pH 8.0 are dried over $K_2CO_3$ and evaporated to dryness under reduced pressure. The obtained crude product is then reduced catalytically or with complex metal hydrides.

The catalytic reduction is carried out at ambient temperature in a high-pressure autoclave at hydrogen pressure of 5 to 70 atm in glacial acetic acid or some other inert solvent at the ratio substrate:catalyst being 1:24 to 1:2. Noble metals or their oxides, e.g. Rh/C or $PtO_2$, can be used as catalysts. After the hydrogenation is completed (2 to 24 hours) the reaction mixture is filtered, the filtrate is evaporated to a thick syrup under reduced pressure, the residue is dissolved in water and extracted several times with dichloromethane or chloroform at pH 6.0, 6.5 and 8.3. The combined extracts at pH 8.3 are dried over $K_2CO_3$ and evaporated to dryness.

The reduction with complex metal hydrides, e.g. sodium borohydride, is carried out by gradually adding solid $NaBH_4$ (over about 4 hours) at 4° C. to a methanolic solution of the crude product, obtained by means of Beckmann rearrangement of erythromycin A oxime, and thereafter crude 11-aza-10-deoxo-10-dihydroerythromycin A is isolated by conventional methods. The obtained precipitate is suspended in ether, stirred for about 2 hours under ice-cooling, filtered and the filtrate is evaporated as chromatographically (dimethyl formamide: methanol 3:1) pure compound I.

It has also been found that by acylation of the compound I with acid anhydrides of the formula $R_I$-—CO—O—$COR_{II}$, wherein $R_I$ and $R_{II}$ represent lower alkyl radicals, the corresponding 2',N-diacyl derivatives (II), 2',4", N-triacyl derivatives (III) and 2′,4″,13,N-tetraacyl derivatives (IV) can be obtained. The reaction is carried out, depending on the anhydride used, at a temperature from 0° to 25° C. in pyridine as solvent and the isolation is carried out by conventional methods (J. Med. Chem. 15, 631, 1972). The corresponding N-acyl derivatives (V) can be prepared by hydrolysis of 2′,N-diacyl derivatives in methanol with 5% w/w aqueous NaHCO$_3$ solution.

By the reaction of the compound I with ethylene carbonate in the presence of K$_2$CO$_3$ in toluene, ethyl acetate or some other inert solvent, 11-aza-10-deoxo-10-dihydroerythromycin A cyclic 13,14-carbonate (VI) is obtained, which by acylation with acid anhydrides of the formula R$_I$CO—O—COR$_{II}$, wherein R$_I$ and R$_{II}$ have the meanings as defined above, gives the corresponding acyl derivatives (VII).

By the reaction of the compound I with 2 to 6 moles of sulfochlorides of the formula 4—R—C$_6$H$_4$—SO$_2$Cl, wherein R represents alkyl, halogen or acylamino group, in the presence of a double amount of alkalis, e.g. Na$_2$CO$_3$, in acetone or some other similar solvent, N—(4—R—benzenesulfonyl) derivatives of the compound I (VIII) are obtained, wherein R has the meaning as defined above.

In order to examine the antibacterial action, some new compounds were tested in vitro on a series of gram-positive and gram-negative micro-organisms. The results are shown in Table 1 as minimum inhibitory concentrations (MIC) in mcg/ml in comparision with erythromycin A erythromycin A oxime.

TABLE 1

| Test bacterium strain | E | EO | I | III | IV | VI | VIII |
|---|---|---|---|---|---|---|---|
| Streptococcus faecalis ATCC 8043 | 0.05 | 0.05 | 0.5 | 125 | 175 | 0.05 | 20 |
| Staphylococcus epidermidis ATCC 12228 | 0.1 | 0.1 | 0.5 | 200 | 200 | 2.5 | 100 |
| Staphylococcus aureus ATCC 6538-P | 0.5 | 0.5 | 0.5 | 150 | 200 | 1.0 | 100 |
| Micrococcus flavus ATCC 10240 | 0.05 | 0.1 | 0.05 | 50 | 175 | 0.5 | 20 |
| Sarcina lutea ATCC 9341 | 0.05 | 0.05 | 0.05 | 10 | 10 | 0.1 | 50 |
| Bacillus cereus var. mycoides ATCC 11778 | 0.1 | 0.1 | 0.5 | 200 | 175 | 2.5 | 50 |
| Bacillus subtilis ATCC 6633 | 0.05 | 0.1 | 5 | 175 | 200 | 0.5 | 100 |
| Corynebacterium xerosis NCTC 9755 | 0.1 | 0.1 | 1.0 | — | — | — | — |
| Brucella bronchiseptica ATCC 4617 | 1.0 | 1.0 | 1.0 | — | — | — | — |
| Pseudomonas aeruginosa NCTC 10490 | 50 | 50 | 50 | — | — | — | — |
| Klebsiella pneumoniae ATCC 10031 | 5.0 | 5.0 | 10 | — | — | — | — |
| Escherichia coli ATCC 10536 | 25 | 25 | 10 | — | — | — | — |
| Shigella flexneri II-1819/C | 25 | 50 | 10 | — | — | — | — |
| Salmonella panama | 50 | 50 | 50 | — | — | — | — |

E erythromycin A
EO erythromycin A oxime
— not determined
Roman numbers refer to novel compounds from Examples.

At examination of acute i.v. toxicity in albino mice by method of Litchfield-Wilcoxon, it has been found that 11-aza-10-deoxo-10-dihydroerythromycin A is less toxic that the starting erythromycin A oxime (Table 2).

TABLE 2

|  | EO | I |
|---|---|---|
| (LD$_{50}$) mg/kg | 74 | 110 |

EO erythromycin A oxime

The stability in acid medium of the novel compounds was determined by exposing them to the action of 1 N HCl for 30 minutes, 1 hour, 2 hours, 3 hours and 6 hours at pH 1.2, followed by the determination of minimum inhibitory concentrations on test strain Staphylococcus aureus ATCC 6538-P and it has been found that the stability of the novel compounds I and VI is within the range of that of the starting antibioticum erythromycin A oxime, they are, however, significantly more stable than erythromycin A (Table 3).

TABLE 3

| Exposure time in hours | MIC (mcg/ml) | | | |
|---|---|---|---|---|
|  | E | EO | I | VI |
| 0 | 0.5 | 0.1 | 0.5 | 1.0 |
| ½ | 7.5 | 0.1 | 0.5 | 1.0 |
| 1 | 10 | 0.1 | 0.5 | 1.0 |
| 2 | 10 | 0.5 | 1.0 | 2.5 |
| 3 | 10 | 0.5 | 1.0 | 2.5 |
| 6 | 20 | 0.5 | 1.0 | 2.5 |

E erythromycin A
EO erythromycin A oxime
Roman numbers refer to the novel compounds from the Examples.

The invention is illustrated by the following Examples, which are not to be considered a limitation thereof.

EXAMPLE 1

Beckmann rearrangement of erythromycin A oxime p-toluenesulfochloride (6.16 g, 0.032 mole) in acetone (70 ml) and HaHCO$_3$(5.4 g, 0.064 mole) in water (245 ml) was dropped into a solution of erythromycin A oxime (12 g, 0.016 mole) in acetone (200 ml) for 2 hours at the temperature of 5° C. whilst stirring. The reaction mixture was stirred at this temperature for an additional two hours, acetone was evaporated under reduced pressure. To the obtained suspension, CH$_2$Cl$_2$ (50ml) was added. The reaction mixture with pH 7.9 was acidified with 1 N HCl to pH 5.5. The layers were separated and the aqueous acidic layer was extracted with CH$_2$Cl$_2$ (2×50 ml). The extraction with dichloromethane was repeated at pH 6 (3×50 ml) and at pH 8 (5×100 ml). The combined dichloromethane extracts were dried over K$_2$CO$_3$ and evaporated to dryness under reduced pressure. At pH 8, a product (8.4 g) with the following physical constants was isolated:

M.p. 128°–131° C.
$[\alpha]_D^{20} = -54.63°$ (1% CH$_2$Cl$_2$).
IR(CHCl$_3$) 1705 and 1725 cm$^{-1}$.
$^{13}$C NMR(CDCl$_3$) 163.9 ppm.
M+ 730.

EXAMPLE 2

11-aza-10-deoxo-10-dihydroerythromycin A (I)/Method A

The crude product of Example 1 (6.0 g, 0.008 mole) was dissolved in glacial acetic acid (60 ml). PtO$_2$ (0.25 g) was added and the hydrogenation took place for 2 hours at ambient temperature and a pressure of 70 atm whilst stirring. The catalyst was filtered off. The filtrate was evaporated to a thick syrup under reduced pressure, dissolved in water (160 ml) and then extracted with CH$_2$Cl$_2$ at pH 6.0 and 6.5 (3×50 ml) and at pH 8.3

(3×100 ml). The combined extracts at pH 8.3 were dried over $K_2CO_3$ and evaporated to dryness under reduced pressure. Chromatographically (dimethyl formamide:methanol 3:1) pure 11-aza-10-deoxo-10-dihydroerythromycin A (4.8 g) was obtained.

M.p. 113°–116° C.

$[\alpha]_D^{20} = -33.91°$ (1% $CH_2Cl_2$).

IR($CHCl_3$) 1725 $cm^{-1}$ (C=O lactone) and 1640 $cm^{-1}$ (—NH—).

$^{13}C$ NMR($CDCl_3$) 56.8 ppm (C—10).

M+ 734.

EXAMPLE 3

11-aza-10-deoxo-10-dihydroerythromycin A (I)/Method B

The crude product of Example 1 (2.0 g) was dissolved in glacial acetic acid (20 ml). 5% w/w Rh/C (1.0 g) was added and the hydrogenation took place for 8 hours at ambient temperature and a pressure of 65 atm whilst stirring. The catalyst was filtered off and the product was isolated by the procedure described in Example 2. A product (1.3 g) with physical constants identical with those of the compound I of Example 2 was obtained.

EXAMPLE 4

11-aza-10-deoxo-10-dihydroerythromycin A (I)/Method C

To a solution of the crude product of Example 1 (12 g, 0.016 mole) in absolute methanol (300 ml), $NaBH_4$ (12 g, 0.316 mole) was added gradually in about 4 hours at 4° C. whilst stirring. After being allowed to stand at ambient temperature for 24 hours, $CO_2$ was introduced until the precipitation was complete. The precipitate obtained was filtered off and the filtrate was evaporated to dryness under reduced pressure. The precipitate was dissolved in $CHCl_3$ (300 ml). The chloroform solution was washed with 10% w/w $NaHCO_3$ solution and water (2×150 ml), dried over $K_2CO_3$, filtered and evaporated to dryness under reduced pressure. The precipitate obtained was dissolved in $CHCl_3$ (100 ml). To the solution water (300 ml) was added. The reaction mixture with pH 11.3 was acidified with 2 N HCl to pH 2.5 and stirred for 15 minutes. With 20% w/w NaOH solution the pH was adjusted to 6.0, the layers were separated and the aqueous layer was extracted with $CHCl_3$ (2×100 ml). The extraction with chloroform was repeated at pH 6.5 (3×50 ml) and at pH 8.3 (5×50 ml), the combined extracts were dried over $K_2CO_3$ and evaporated to dryness under reduced pressure. The precipitate, isolated at pH 8.3, was suspended in dry ether, stirred for 2 hours whilst ice-cooling, filtered and the filtrate was evaporated to give chromatographically (dimethyl formamide: methanol 3:1) pure 11-aza-10-deoxo-10-dihydroerythromycin A. The product obtained was identical with that of Example 2.

EXAMPLE 5

2',N-diacetyl-11-aza-10-deoxo-10-dihydroerythromycin A (II)

To a solution of 11-aza-10-deoxo-10-dihydroerythromycin A (4.0 g, 0.0054 mole) in pyridine (80 ml), acetic anhydride (50 ml, 0.53 mole) was added and the mixture was allowed to stand for 30 minutes at ambient temperature. The reaction was stopped by the addition of ice, pH was adjusted to 9 with 20% w/w NaOH solution and it was extracted with chloroform (3×75 ml). The combined chloroform extracts were washed with water (2×75 ml), dried over $K_2CO_3$ and evaporated to dryness under reduced pressure. The crude precipitate was re-precipitated from ether with petroleum ether. Yield 3.4 g (76.4%).

M.p. 133°–138° C.

$pK_b$ 6.7 (dimethyl formamide (66% v/v)-water).

IR($CHCl_3$) 1725 (C=O lactone and ester), 1610 (—CO—N<) and 1235 $cm^{-1}$ (acetyl).

EXAMPLE 6

2',N-dipropionyl-11-aza-10-deoxo-10-dihydroerythromycin A (II)

From 11-aza-10-deoxo-10-dihydroerythromycin A (2.0 g, 0.0027 mole) and propionic anhydride (25 ml, 0.194 mole), pure (chloroform: methanol 7:3) 2',N-dipropionyl-11-aza-10-deoxo-10-dihydroerythromycin A (1.35 g, 57.6 %) was isolated by the reaction in pyridine (40 ml) according to the procedure described in Example 5.

M.p. 183°–186° C.

$pK_b$ 6.7 (dimethyl formamide (66% v/)-water).

IR($CHCl_3$) 1725 (C=O lactone and ester), 1615 (—CO—N<) and 1175 $cm^{-1}$ (propionyl).

EXAMPLE 7

2',4''-N-triacetyl-11-aza-10-deoxo-10-dihydroerythromycin A (III)

To a solution of 11-aza-10-deoxo-10-dihydroerythromycin A (1.0 g, 0.00136 mole) in pyridine (20 ml), acetic anhydride (20 ml, 0.212 mole) was added and the mixture was allowed to stand for 76 hours at ambient temperature. The reaction was stopped by the addition of ice, the pH of the reaction mixture was adjusted to 9 with 20% w/w NaOH solution and then it was extracted with chloroform (5×30 ml). The combined chloroform extracts were washed with saturated $NaHCO_3$ solution (3×30 ml) and water (2×30 ml) dried over $K_2CO_3$ and evaporated to dryness under reduced pressure. The crude product was purified by precipitation from chloroform with petroleum ether. Pure (chloroform:formamide 100:20:2) triacetyl derivative (0.72 g, 61.5%) was obtained.

M.p. 148°–156° C.

$[\alpha]_D^{20} = -31.5°$ (dimethyl formamide (66% v/v)-water).

IR($CHCl_2$) 1735 (C=O lactone and ester), 1625 (—CO—N<) and 1235 $cm^{-1}$ (acetyl).

Mass spectrometry gave molecular ion M+ 860.

EXAMPLE 8

2',4'',13,N-tetraacetyl-11-aza-10-deoxo-10-dihydroerythromycin A (IV)

A solution of 11-aza-10-deoxo-10-dihydroerythromycin A (1.5 g, 0.002 mole) in pyridine (30 ml) and acetic anhydride (15 ml, 0.159 mole) was allowed to stand for 10 days at ambient temperature and then processed analogously as triacetyl ester in Example 7. After some successive precipitations from chloroform with petroleum ether, 2',4'',13,N-tetraacetyl-11-aza-10-deoxo-10-dihydroerythromycin A (1.42 g, 77%) was obtained.

M.p. 110°–115° C.

$[\alpha]_D^{20} = -35.43°$ (1% $CH_2Cl_2$).

IR($CHCl_3$) 1735 (C=O lactone and ester), 1624 (—CO—N<) and 1240 $cm^{-1}$ (acetyl).

Mass spectrometry gave molecular ion at m/e 902.

EXAMPLE 9

N-propionyl-11-aza-10-deoxo-10-dihydroerythroycin A (V)

The compound II of Example 6 (2.15 g, 0.00254 mole) was dissolved in methanol (45 ml), 5% w/w NaHCO$_3$ solution (45 ml) was added and it was allowed to stand for 7 days at ambient temperature. Methanol was evaporated under reduced pressure, the pH of the aqueous suspension was adjusted to 9 with 20% w/w NaOH solution and then extracted with CHCl$_3$ (3×50 ml). The combined chloroform extracts were washed with water (2×50 ml), dried over K$_2$CO$_3$ and evaporated to dryness under reduced pressure. Yield 1.84 g (92.6%).

M.p. 122°–129° C.

pK$_b$ 8.6 (dimethyl formamide (66% v/v)-water).

IR(CHCl$_3$) 1720 (C=O lactone), 1610 (—CO—N<).

EXAMPLE 10

11-aza-10-deoxo-10-dihydroerythromycin A cyclic 13,14-carbonate (VI)

11-aza-10-deoxo-10-dihydroerythromycin A (1.0 g, 0.00136mole) was dissolved in ethyl acetate (10 ml). To the solution, K$_2$CO$_3$ (0.2 g, 0.0014 mole) and ethylene carbonate (0.5 g, 0.00568 mole) were added and then it was boiled for 2 hours under reflux condenser. The reaction mixture was cooled, filtered and then evaporated to thick oil under reduced pressure, from which upon the addition of water (about 25 ml) 11-aza-10-deoxo-10-dihydroerythromycin A cyclic 13,14-carbonate (0.85 g, 82.1%) was precipitated.

M.p. 129°–135° C.

IR(CHCl$_3$) 1790 (C=O carbonate), 1725 (C=O lactone).

M+ 760.

EXAMPLE 11

2',4'',N-triacetyl-11-aza-10-deoxy-10-dihydroerythromycin A cyclic 13,14-carbonate (VII)

11-aza-10-deoxo-10-dihydroeryromycin A cyclic 13,14-carbonate (0.5 g, 0.00065 mole) was dissolved in pyridine (2.5 ml). To the solution, acetic anhydride (2.5 ml, 0.00265 mole) was added and it was allowed to stand for 28 hours at ambient temperature. The reaction was stopped by addition of ice and the product was extracted with CHCl$_3$ (3×15 ml). The combined chloroform extracts were washed with water (2×10 ml), dried over K$_2$CO$_3$ and evaporated to dryness under reduced pressure.

Yield 0.58 g.

M.p. 109°–117° C.

IR(CHCl$_3$) 1800 (C=O carbonate), 1730 (C=O lactone and ester) and 1625 (—CO—N<) and 1240 cm$^{-1}$ (acetate).

$^1$H NMR(CDCl$_3$) 2.06(3H), 2.12(3H), 2.12(3H), 2.3(6H) and 3.3(3H) ppm.

EXAMPLE 12

N-(4-methyl-benzenesulfonyl)-11-aza-10-deoxo-10-dihydroerythromycin A (VIII)

To a solution of 11-aza-10-deoxo-10-dihydroerythromycin A (4.0 g, 0.0054 mole) in dry acetone (120 ml), Na$_2$CO$_3$·H$_2$O (13.8 g, 0.11 mole) was added and then a solution of p-toluenesulfochloride (6.24 g, 0.0327 mole) in dry acetone (120 ml) was added under vigorous stirring and it was boiled under reflux condenser for 12 hours. The reaction mixture was filtered and the filtrate was evaporated to dryness under reduced pressure. The precipitate was dissolved in 100 ml CH$_2$Cl$_2$. To the solution, water (40 ml) was added (pH of the obtained solution being 7). The pH was adjusted to 6 with 1 N HCl, the layers were separated and the aqueous layer was extracted with CH$_2$Cl$_2$ (3×40 ml). After drying the combined dichloromethane extracts over K$_2$CO$_3$ and evaporated the solvent, a crude product (3.6 g) was obtained, which was purified by chromatography on a silicagel column.

M.p. 150°–153° C.

[α]$_D^{20}$ = −9.04° (1% CH$_2$Cl$_2$).

IR(CHCl$_3$) 1730 (C=O lactone), 1600, 755 and 655 (p-phenyl) and 1340 cm$^{-1}$ (—SO$_2$—).

Mass spectrometry gave molecular ion at m/e 888.

what is claimed is:

1. Compound having the structural formula:

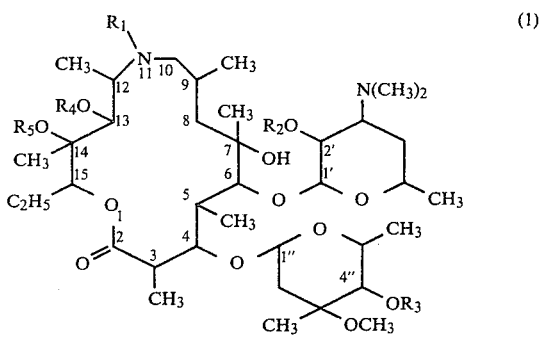

(1)

wherein R$_1$ represents hydrogen, lowr alkanoyl or 4—R—C$_6$H$_4$—SO$_2$—, wherein R represents an alkyl, and each R$_2$, R$_3$, R$_4$ and R$_5$ individually represents hydrogen or lower alkanoyl or R$_4$ and R$_5$ together are >C=O.

2. A compound according to claim 1, wherein each R$_1$, R$_2$, R$_3$, R$_4$ and R$_5$ is hydrogen.

3. A compound according to claim 1, wherein each R$_1$ and R$_2$ represents lower alkanoyl and each R$_3$, R$_4$ and R$_5$ represents hydrogen.

4. A compound according to claim 1, wherein each R$_1$, R$_2$ and R$_3$ represents lower alkanoyl and each R$_4$ and R$_5$ represents hydrogen.

5. A compound according to claim 1, wherein each R$_1$, R$_2$, R$_3$ and R$_4$ represents lower alkanoyl and R$_5$ represents hydrogen.

6. A compound according to claim 1, wherein R$_1$ represents lower alkanoyl and each R$_2$, R$_3$, R$_4$ R$_5$ represents hydrogen.

7. A compound according to claim 1, wherein each R$_1$, R$_2$, and R$_3$ represents hydrogen and R$_4$ and R$_5$ together are >C=O.

8. A compound according to claim 1, wherein R$_1$ represents 4—R—C$_6$H$_4$—SO$_2$— and each R$_2$, R$_3$, R$_4$ and R$_5$ represents hydrogen.

9. A compound according to claim 1, wherein each R$_1$, R$_2$, R$_3$ represents lower alkanyol and R$_4$ and R$_5$ together are >C=O.

10. A process for the preparation of the compound of claim 1 which comprises subjecting erhthromycin A oxime to Beckmann rearrangement, subjecting the product obtained from said Beckmann rearrangement to reduction, and then subjecting the product obtained by said reduction to O- or N-acylation.

11. A process according to claim 10, wherein the Beckmann rearrangement is carried out using 1 to 2 moles of sulfochlorides of the formula 4—R—C$_6$H$_4$—SO$_2$Cl or hydrogen, wherein R represents alkyl, and 2 to 4 moles of alkali metal salts of 5° C. in a mixture of acetone and water.

12. A process according to claim 11, wherein the product obtained by said rearrangement is reduced catalytically or with complex metal hydrides to give 11-aza-10-deoxo-10-dihydroerythromycin A of the formula (1), wherein each R$_1$, R$_2$, R$_3$, R$_4$ and R$_5$ represents hydrogen.

13. A process according to claim 10 or 12, wherein the catalytic reduction is carried out in an inert solvent in the presence of noble metals or their oxides as catalysts at ambient temperature and at a pressure of 5 to 70 atm.

14. A process according to claim 10 or 12, werein the reduction is carried out in absolute alcohol, with complex metal hydride, at a temperature of about 4° C.

15. A process according to claim 11 or 12, wherein the 11-aza-10-deoxo-10-dihydroerthromycin A obtained by said rearrangement is reacted with acid anhydride of the formula R$_I$—CO—O—COR$_{II}$, wherein each R$_I$ and R$_{II}$ represents lower alkyl to give O,N-di-lower alkanoyl, O,N-tri-lower alkanoyl and O,N-lower alkanoyl, O,N-tri-lower alkanoyl and O,N-tetra-lower alkanoyl compounds of formula (1), wherein each R$_1$ and R$_2$ represents lower alkanoyl, each R$_3$ and R$_4$ represents hydrogen or lower alkanoyl and R$_5$ represents hydrogen.

16. A process according to claim 11 or 12, wherein the 11-aza-10-deoxo-10-dihydroerythromycin A obtained is reacted with ethylene carbonate in the presence of K$_2$CO$_3$ in ethyl acetate to give 11-aza-10-deoxo-11-dihydroerythromycin A cyclic 13,14-carbonate of the formula (1), wherein each R$_1$, R$_2$ and R$_3$ represents hydrogen and R$_4$ and R$_5$ together are carbonyl.

17. A process according to claim 16, wherein the 11-aza-10-deoxo-10-dihydroerythromycin A cyclic 13,14-carbonate obtained is reacted with acid anhydride of the formula R$_I$CO—O—COR$_{II}$, wherein each R$_I$ and R$_{II}$ represents lower alkyl to give lower alkanoyl compounds of formula (1), wherein each R$_1$, R$_2$ and R$_3$ represents lower alkanoyl and R$_4$ and R$_5$ together are carbonyl.

18. A process according to claim 11 or 12, wherein the 11-aza-10-deoxo-10-dihydroerythromycin A obtained is reacted with sulfochloride of the formula 4—R—C$_6$H$_4$—SO$_2$Cl, wherein R represents alkyl in acetone in the presence of alkali to give sulfonamide of formula (1), wherein R$_1$ represents 4—R—C$_6$H$_4$—SO$_2$—, and each R$_2$, R$_3$, R$_4$ and R$_5$ is hydrogen.

19. The process of claim 13 wherein said inert solvent is glacial acetic acid.

20. The process of claim 14 wherein said alcohol is methanol.

21. The process of claim 20 wherein said hydride is NaBH$_4$.

22. The process of claim 14 wherein said hydride is NaBH$_4$.

23. A process according to claim 15 wherein the O,N-di-lower alkanoyl derivative of 11-aza-10-deoxo-10-dihydroerthromycin A obtained is subjected to hydrolysis or methanolysis to provide N-lower alkanoyl derivatives of formula (1) wherein R$_1$ represents lower alkanoyl and each R$_2$, R$_3$, R$_4$ and R$_5$ represents hydrogen.

24. The process of claim 18 wherein said alkali is Na$_2$CO$_3$.

* * * * *